United States Patent
Wong et al.

(10) Patent No.: US 7,393,329 B1
(45) Date of Patent: Jul. 1, 2008

(54) METHOD AND APPARATUS FOR DELIVERING RADIATION THERAPY DURING SUSPENDED VENTILATION

(75) Inventors: John W. Wong, Bloomfield, MI (US);
David A. Jaffray, Windsor (CA);
Michael B. Sharpe, Windsor (CA);
John R. Musselwhite, Tecumseh (CA)

(73) Assignee: William Beaumont Hospital, Royal Oak, MI (US)

( * ) Notice: Subject to any disclaimer, the term of this patent is extended or adjusted under 35 U.S.C. 154(b) by 484 days.

(21) Appl. No.: 09/424,431

(22) PCT Filed: May 22, 1998

(86) PCT No.: PCT/US98/10389

§ 371 (c)(1),
(2), (4) Date: Mar. 16, 2001

(87) PCT Pub. No.: WO98/52635

PCT Pub. Date: Nov. 26, 1998

Related U.S. Application Data

(60) Provisional application No. 60/063,454, filed on May 23, 1997.

(51) Int. Cl.
*A61B 5/08* (2006.01)
(52) U.S. Cl. .................. 600/534; 600/428; 128/916
(58) Field of Classification Search ........... 128/898, 128/916; 600/534, 428, 407
See application file for complete search history.

(56) References Cited

U.S. PATENT DOCUMENTS

| | | | | | |
|---|---|---|---|---|---|
| 3,871,360 | A | * | 3/1975 | Van Horn et al. | 378/95 |
| 4,387,722 | A | * | 6/1983 | Kearns | 378/95 |
| 4,752,064 | A | * | 6/1988 | Voss | 5/638 |
| 4,815,459 | A | * | 3/1989 | Beran | 128/207.14 |
| 4,939,757 | A | * | 7/1990 | Nambu | 378/8 |
| 5,067,494 | A | * | 11/1991 | Rienmueller et al. | 378/8 |
| 5,111,809 | A | * | 5/1992 | Gamble et al. | 128/204.18 |
| 5,287,851 | A | * | 2/1994 | Beran et al. | 128/204.23 |
| 5,479,920 | A | * | 1/1996 | Piper et al. | 128/204.23 |
| 5,485,833 | A | * | 1/1996 | Dietz | 128/204.23 |
| 5,511,553 | A | * | 4/1996 | Segalowitz | 128/903 |
| 5,876,352 | A | * | 3/1999 | Weismann | 600/529 |
| 5,915,381 | A | * | 6/1999 | Nord | 128/204.21 |
| 5,950,631 | A | * | 9/1999 | Donaldson et al. | 128/898 |
| 6,148,814 | A | * | 11/2000 | Clemmer et al. | 128/200.24 |
| 6,436,127 | B1 | * | 8/2002 | Anderson et al. | 607/89 |
| 6,571,796 | B2 | * | 6/2003 | Banner et al. | 128/204.26 |
| 6,597,939 | B1 | * | 7/2003 | Lampotang et al. | 600/427 |

* cited by examiner

*Primary Examiner*—Michael J. Hayes
*Assistant Examiner*—Michael G. Mendoza
(74) *Attorney, Agent, or Firm*—Brinks Hofer Gilson & Lione

(57) ABSTRACT

Methods and apparatus for delivering radiation therapy to patients during suspended ventilation are provided. The apparatus includes a ventilator assembly having first and second selectively operable valves that independently control inhalation and exhalation of the patient. Both valves are shut to suspend patient ventilation for a period of time. In the methods of the present invention, radiation therapy is administered during this period of suspended patient ventilation.

17 Claims, 3 Drawing Sheets

METHOD AND APPARATUS FOR DELIVERING RADIATION THERAPY DURING SUSPENDED VENTILATION

This application claims priority under 35 U.S.C. § 111(b) to the filing date of U.S. Provisional Application 60/063,454, May 23, 1997, of the same title.

BACKGROUND OF THE INVENTION

1. Field of the Invention

The present invention relates generally to a method and apparatus for delivering radiation therapy. More particularly, the present invention relates to a method and apparatus for delivering radiation therapy during suspended ventilation.

2. Discussion

Radiation for the treatment of cancer embodies a variety of risks related to overexposure to healthy tissue. A major concern in increasing the dose to treat cancer is the potential increase in life-threatening complications. This is particularly the case for treatment in the thoracic and upper abdominal regions. Because of respiratory motion, a large margin is needed to ensure proper tumor coverage, which in turn leads to a large volume of healthy tissue being irradiated. For lung treatment, there is a risk of five percent pneumonitis in five years if the whole lung receives more than 1,750 cGy, two-thirds of the lung receives more than 3,000 cGy, and one-third of the lung receives 4,500 cGy. Similar observations have been made for other sites, such as the treatment of focal lesions in the liver.

There are rather difficult tolerances to satisfy if one wants to increase dose. Take, for example, the traditional radiation treatment using AP/PA (anterior to posterior/posterior to anterior) beam arrangements for lung treatment. Given, for example, a modest lung thickness of 15 cm. Assuming a total lung capacity of 5.0 liters, the total irradiated lung volume is calculated by taking the lung volume around the tumor and subtracting tumor volume. Given a margin of 3 cm around the tumor that is 7 cm in diameter, 45% of the lung will initially be irradiated. Given a margin of 2 cm, 30% of the lung will be irradiated. Given a margin of 1 cm, 18% of the lung will be irradiated. Given a margin of 0.5 cm, 13% of the lung will be irradiated.

In response to concerns regarding over-exposure, there have been intense efforts over the past decade to implement high dose conformal radiation therapy which have led to the development of many new advanced technologies. These advanced technologies include computed tomographic (CT) simulation, three dimensional (3D) treatment planning, computer controlled medical accelerators, multileaf collimators (MLCs), and electronic portal imaging devices (EPIDs). These technologies are becoming increasingly more common, making possible the implementation of new treatment techniques such as intensity modulated radiation therapy. The success of high dose conformal therapy depends critically on treatment accuracy. With more accurate information about the position of a tumor, a tighter treatment margin can be prescribed such that a higher dose can be delivered to the tumor without increasing deleterious complications.

In practice, the treatment margin must account for the width of the beam penumbra, the daily variation in patient setup, and the variation in organ positions between fractions and during a single fraction. Recent advances have been made to sharpen beam penumbra, reduce daily setup variation and compensate for inter-fraction variation of organ position. (Intra-fraction organ motion associated with breathing, however, remains problematic.) Intra-fraction variations pertain to the changes in the organ shapes and positions during a single treatment fraction. These include the motion of tumors and organs in the thoracic and abdominal regions. In certain procedures for radiotherapy of the thorax, patient breathing has an effect on the procedure. Motion of the lungs and diaphragm can cause displacement of organs and a tumor being treated. Organs and tumors in the thorax and abdomen are known to move by more than 2 cm during the breathing cycle. At present, the 3D imagings used for treatment planning are "static". They do not contain information about the changing tumor positions while the patient breathes. Consequently, a wide margin is used, irradiating a large volume of critical tissue. As a result, limits are placed upon the dose that can be delivered to the tumor. Concern for pulmonary complications has constrained radiation therapy of lung cancer, despite the dismal prognosis of the disease. High dose conformal therapy in the thorax and abdomen is more effective when organ motion due to breathing can be minimized.

There have been different approaches to minimizing respiratory motion. One approach is to have the patient shallowly breathe pure oxygen. Another approach has been through a technique known as "triggering" or "gating" in which the respiration cycle is monitored using an external device such as a spirometer or a string-gauge to turn on the beam only at a certain point in the respiration cycle. A possible component of this technique is to train the patient to exercise the breath-holding at the appropriate lung volume in order to extend the duty cycle of the beam. A further approach is to use deep inspiration breath holding, during which time the beam is activated.

The optimal delivery of gated or "breath-hold" therapy requires the 3D characterization of dynamic organ and tumor motion such that both beam geometry and "gate" can be optimized. However, this optional approach is not possible with most gated therapy proposals which rely on 2D fluoroscopy. It is also difficult to obtain gated 3D CT scans because of the complexity in machine control. Deep inspiration breath hold can be applied, but the 3D CT scan can only be made in one respiratory position. It is possible that dynamic 3D tomographic images can be made with the Immatron (an ultrafast CT specifically built for cardiac scanning) or using a fast MRI. However, the former approach is prohibitively expensive, while the latter approach produces distortions and complex image fusion is required to provide 3D images.

Accordingly, current approaches to gated therapy rely exclusively on the passive monitoring of respiration, followed by electronic or manual triggering of the beam. However, electronic triggering requires control of the medical accelerator to coordinate with passive respiratory monitoring. This is not readily achieved. On the other hand, manual gating requires the patient to reproducibly get to the same respiratory position. Inevitable variability means that a wider tolerance would need to be set. In addition, the radiation needs to be turned off immediately when the breath-hold creeps out of tolerance. Failure to do so can be serious since gated therapy is likely to employ higher dose rates.

While the above techniques represent various advances in the art, all known methods and devices for the delivery of radiation therapy during suspended ventilation are subject to improvement.

SUMMARY OF THE INVENTION

The method and associated apparatus of the present invention involves attaching a respiration monitor to a patient through a mouth piece that includes air flow valve(s). Computer control provides a measure of the cyclical expiration and inhalation cycle of the patient. When a desired point in the respiration cycle point is reached by the patient, the mouthpiece valve(s) is/are operated to suspend or "freeze" patient breathing at the desired point. In other words, all air flow through the mouth piece is stopped at the desired point. While the valve(s) is/are closed, the patient cannot inhale or exhale. In some cases, several cycles of this breath "freezing" can be used to administer the desired therapeutic radiation dosage. Since the clinician controls the point at which breath freezing occurs, the patient does not have to produce a repeated breathing state. This approach also does not require a complex interconnection between the respiration monitor and radiation therapy equipment. The system is well suited for low cost implementation with a minimal need to interface with the radio therapy manufacturers and equipment.

It is a principal object of the present invention to provide a method and an apparatus which overcome the drawbacks associated with the prior art, including but not limited to those discussed above.

It is another object of the present invention to provide a method and apparatus for eliminating inaccuracy encountered during diagnosis and therapy attributable to movement of body organs resulting from normal breathing.

It is a more specific object of the present invention to provide a method and apparatus for the delivery of radiation therapy during periods of suspended ventilation.

It is another object of the present invention to provide a method and apparatus which allows for CT planning and treatment at a reproducible ventilatory phase.

The above and other objects are achieved in accordance with the principles of the present invention in a method and apparatus for delivering radiation therapy during suspended ventilation.

In one form, the present invention provides a method to suspend ventilation of a patient for the delivery of radiation therapy. The method includes the general step of identifying a specific air flow direction and lung volume. Additionally, the method of the present invention includes the general step of suspending patient ventilation at the specific air flow direction and lung volume. Further, the method of the present invention includes the general step of administering radiation therapy during the suspension of patient ventilation.

BRIEF DESCRIPTION OF THE DRAWINGS

Additional objects and advantages of the present invention will become apparent from a reading of the following detailed description of the preferred embodiments which makes reference to the drawings of which.

DETAILED DESCRIPTION OF THE INVENTION

Figure 1:
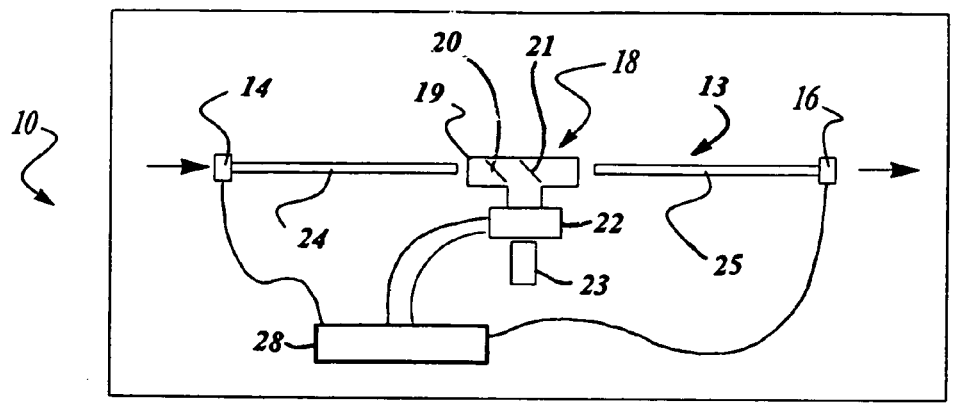
FIG. 1 is a schematic representation of an active breathing control apparatus embodying the present invention for suspending ventilation for purposes of administering radiation therapy.

Referring to FIG. 1, a schematic diagram of an active breathing control apparatus 10 constructed in accordance with the teachings of the present invention is shown.

The active breathing control apparatus utilizes a ventilator assembly 13. (A suitable ventilator for modification is commercially available from Siemens.) As shown, the apparatus has two "scissors" valves 14 and 16 to monitor and control inhalation and exhalation independently. During normal operation, one of the valves 14 or 16 is always closed while the other is open. With the modifications made pursuant to the present invention, the scissors valves 14 and 16 are interfaced to a personal computer (PC) (not shown). The signals are processed to display the changing lung volume during the breathing cycle. A software utility is implemented to allow the user to specify (1) the point in the breathing cycle for closing both valves 14 and 16, and (2) the duration of the active breath-hold.

The patient 12 is interconnected to the modified ventilator assembly 13 through a subassembly 18 which includes a t-connector 19 which includes a first one-way valve 20 and a second one-way valve 21, a pneumotach 22 and a mouthpiece 23. A first tube 24 connects the scissor valve 14 and a second tube 25 connects to the other scissor valve 16. A nose clip 26 is used to prevent ventilation through the nose. Alternatively, the mouthpiece and nose clip 26 can be replaced by a face mask.

The valves 14 and 16 as well as the pneumotach 22 are connected to a computer 28 which selectively drives each element according to a selected operations program.

Figure 2:
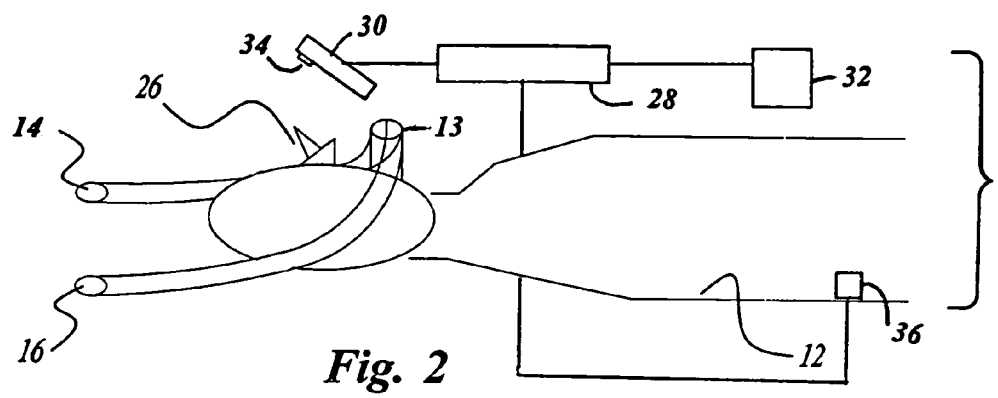
FIG. 2 is a stylized view showing the active breathing control apparatus of the present invention in operative association with a supine patient.

FIG. 2 illustrates the apparatus of the present invention in relation to a supine patient 12. The ventilator assembly 13 is illustrated in its approximate position in relation to the patient 12. Optionally, a mirror 30 is provided at an angle such as a 45 degree angle for the view of the patient 12. A monitor 32 is preferably provided outside of the treatment room for the operator, while a smaller monitor 34 (or LCD) is optionally provided for viewing by the patient. The monitors 32 and 34 provide a means of continuously displaying the cyclical lung volume trace and the target respiration level while the supine patient is breathing. (The displays need not present the same information.) Each of the monitors 32 and 34 is operatively associated with the computer 28. An abort switch 36 may also be provided for operation by the patient 12 to turn off the radiation machine and open the valve 14 in the event of discomfort.

Figure 3:
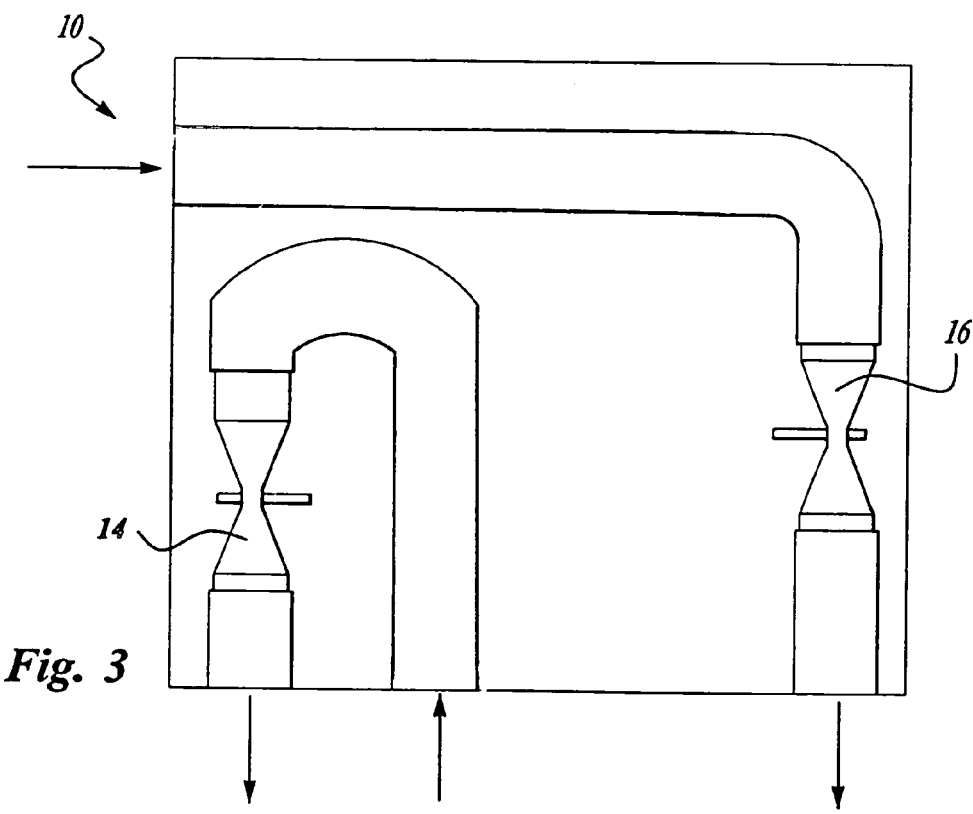
FIG. 3 is a top view of an apparatus constructed in accordance with the teachings of the present invention.

FIG. 3 illustrates is the arrangement of the "scissors" valves 14 and 16 of the active breathing control apparatus 10 within the ventilator assembly 13.

Figure 4:
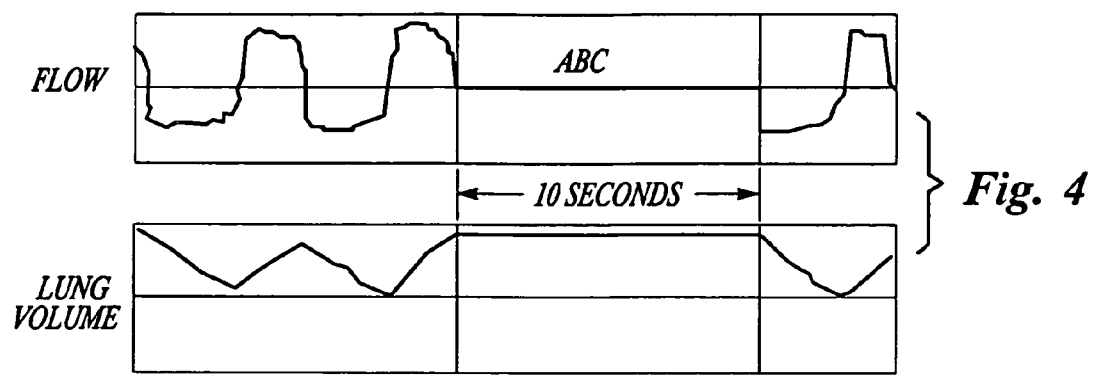
FIG. 4 is a graph plotting air flow and lung volume versus time including a period of suspended ventilation for the delivery of radiation therapy.

FIG. 4 shows the real-time display of the airflow and lung volume for a normal subject during normal breathing. An active breathing control level is also shown.

Figure 5:
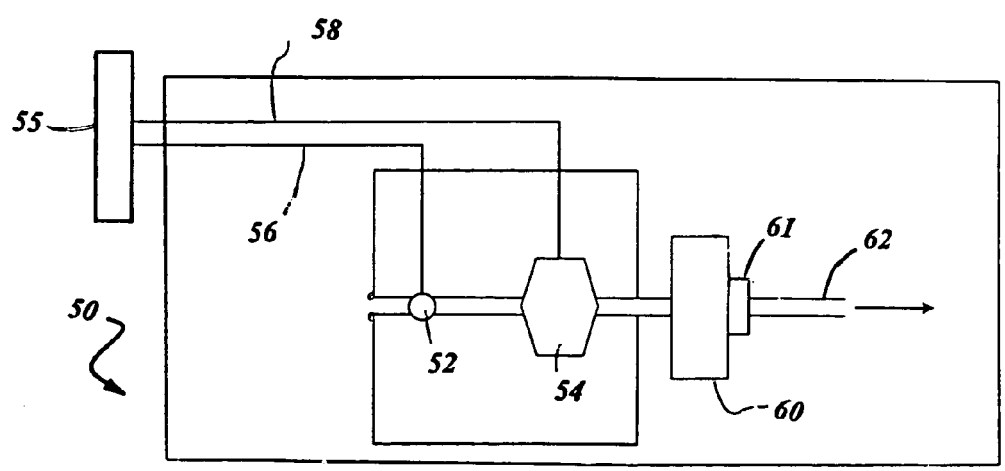
FIG. 5 is a schematic of an alternate embodiment of the apparatus of the present invention.

FIG. 5 illustrates an alternate embodiment of the active breathing control apparatus of the present invention. According to this embodiment, a control apparatus 50 is shown. The apparatus includes a single valve 52 and a pneumotach 54 to monitor and control inhalation and exhalation. The valve 52 and the pneumotach 54 are connected to a computer 55 via lines 56 and 58. The pneumotach 54 is also fluidly connected to a carbon dioxide remover 60 and a millipore filter 61. The carbon dioxide remover 60 may be of the "soda lime" reservoir type, although this is not intended as being limiting.

Figure 6:
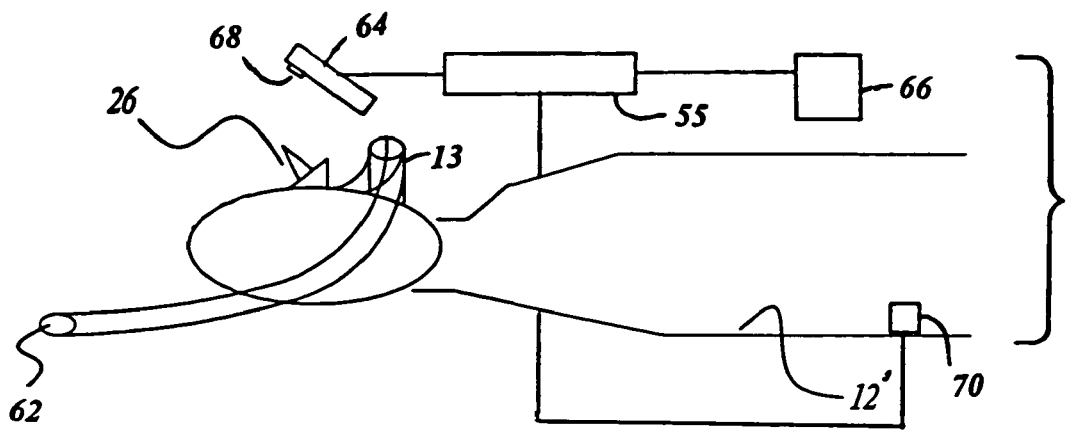
FIG. 6 is a stylized view showing the alternative embodiment of the active breathing control apparatus of the present invention shown in FIG. 5 in operative association with a supine patient.

FIG. 6 illustrates the apparatus 50 in operative association with a supine patient 12'. The patient 12' is provided with a noseclip 26. A mouthpiece 13' is used for ventilation. The fluid line 62 is connected with the millipore filter 61 via the fluid tube 62. Optionally, a mirror 64 is provided at an angle such as a 45 degree angle for the view of the patient 12'. A monitor 66 is preferably provided outside of the treatment room for the operator, while a smaller personal monitor (or LCD) 68 is optionally provided for viewing by the patient. Both the monitor 66 and the personal monitor 68 are operatively associated with the computer 55. An abort switch 70 may also be provided for operation by the patient 12' to turn off the radiation machine and open the valve 52 in the event of discomfort.

In comparison to the two valve system set forth previously, the single valve is simpler to operate. However, the two valve system allows the provision of oxygen to the patient via the valve 14. The single-valve modification also avoids the excessive piping used and significantly shortens the length of tubing, thereby greatly reducing the dead-space where air can be compressed. This modified design also improves the precision of volume measurements.

An apparatus is thus provided which allows for the maintenance of breath-holding reproducibility while being as non-intrusive to the patient as possible. In general operation, and the patient lies in a supine position on a rigid surface tabletop. Breathing through the nose is restricted by the nose-clip. One end of the bi-directional pneumotachnometer is connected to the patient via the mouthpiece while the other is connected to the scissors valve (one or two valves, depending on the embodiment) which controls airflow. Airflow to and from the patient passes through a "soda lime" reservoir to remove exhaled carbon dioxide in the apparatus of the present invention. Adopting standard respiratory care procedures, a millipore filter is preferably used as a barrier against air-borne contaminants. To ease patient burden, the patient is allowed to nose breathe after each sequence of maneuvers which takes no more than 5 minutes.

Regardless of the embodiment, the apparatus is calibrated for flow and volume measurements based on acceptable hospital standards. The output of the pneumotachnometer is interfaced with a Pentium class PC. The flow signal is processed to calculate the changing lung volume during breathing in real-time. Operation of the scissor valve(s) is done under computer control. Software utilities are implemented to allow the user to select the lung volume and flow direction for closing the valve(s). A separate "arming" utility is engaged and allows the user to specify a time delay for activating the system. For example, zero time delay means that the valve is closed at the immediate next instance when the pre-selected parameters are met. A six-second time delay means adding six seconds to the zero time delay. This utility helps coordinate application of the apparatus of the present invention for those radiation machines that operate with a short warm-up prior to beam on, such as a CT scanner or an accelerator such as the Elekta-Philips SL-20.

For each patient, an operating reference needs to be reestablished to set the desired respiratory phase for the apparatus. The functional residual capacity (FRC) of the lungs at the end of normal expiration is chosen because it is the most stable lung volume during normal breathing. At FRC, the lungs are at a natural resting position with neutral pressure. At the start of each session, the supine patient will first go through a period of normal breathing to establish a stable breathing pattern. After that, the volume signals at FRC are averaged for one minute, equivalent to 12 to 15 breathing cycles, and then set as the "zero volume reference." With this zero reference, lung volumes at either inspiration or expiration can be specified for the method of the present invention. Provided that the patient has not moved between maneuvers, the zero reference only needs to be established once.

During an initial training session using the present apparatus, the period of active breath hold that can be comfortably maintained by each individual patient is determined. The period is used for subsequent CT scanning and treatment, but is adjusted as necessary. When the supine patient breathes in and out through the apparatus of the present invention, the cyclical lung volume trace and the target level is displayed continuously on a monitor for the user outside of the treatment room. Inside the treatment room, the patient is shown a similar display and the countdown of the breath-hold period via an angled mirror (such as a 45 degree angle). The patient is also optionally provided with an "abort" switch to turn off the radiation machine and open the valve of the apparatus in case of discomfort. Verbal communication with the patient is maintained throughout the procedure.

Figure 7:
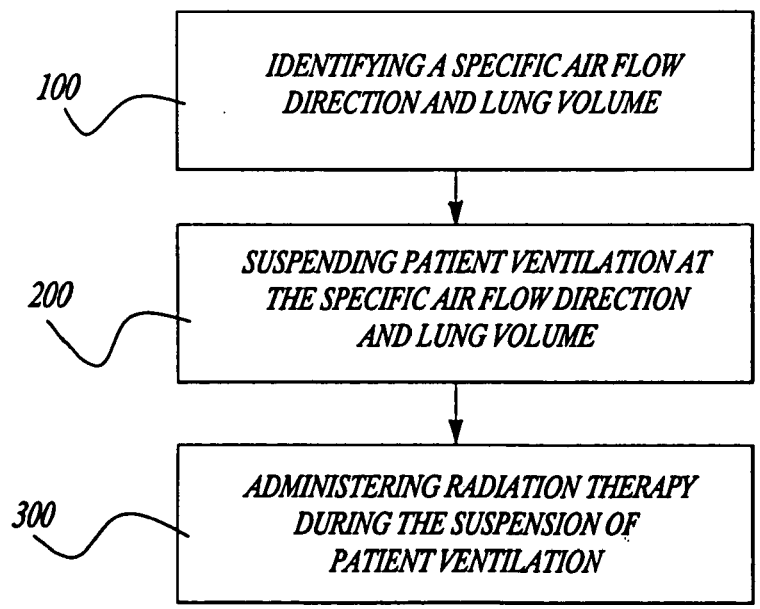
FIG. 7 is a simplified flow chart illustrating the general steps of the method of the present invention.

Turning now to FIG. 7, the method of the present invention for delivering radiation therapy during suspended ventilation will now be described with particular reference to the apparatus itself. FIG. 5 is a flow chart illustrating the general steps of the present invention. The method of the present invention includes three general steps.

In a first step 100, a specific air flow direction and lung volume are identified. This identification is conducted with CT scans taken at different phases of suspended ventilation.

In a second step 200, patient ventilation is suspended at the specific air flow direction and lung volume. Ventilation suspension is accomplished by closing the valves. The patient is preferably alerted to impending ventilation suspension to avoid panic.

In a final general step 300, radiation therapy is administered during suspension of patient ventilation. It may be desirable to incorporate mechanisms to discontinue therapy in the event that the patient desires ventilation.

By using the apparatus of the present invention together with the provided method, the positions of the immobilized organs documented in the planning CT can be reproduced during treatment. The treatment margin can therefore be appropriately reduced, enhancing the potential to escalate dose with conformal therapy. Theoretically, CT scans can be acquired according to the present invention at different respiratory phases. The information can then be analyzed to determine an optimal phase for treatment in terms of the separation of the tumor from other critical organs. A 3D organ "movie" can then be produced for evaluation. However, in practice, it is more important to find a respiratory phase which is most comfortable for the patient to maintain repeated breath-hold during treatment using the present invention and described method. Accordingly, as a default, the expiratory phase near tidal volume is selected, i.e., when the patient begins to exhale after taking in a normal breath. This respiratory phase was preferred by the patients in the preliminary studies, particularly for the longer period of breath-hold. Expiration is chosen because it involves mostly passive lung recoil and may offer some reproducibility advantages. It is anticipated that radiation therapy will be administered over an extended period of days. Generally speaking, the patient, upon returning for treatment, will receive radiation treatments at the previously identified flow direction and lung volume. In certain applications, it may be desirable to conduct follow-up diagnosis to confirm the location of the area identified for treatment.

EXAMPLE

The following example illustrates the application of the above-described method and apparatus according to the present invention.

Feasibility studies based on CT scanning have been performed on patients with tumors in the thorax and abdomen. Helical CT scans were acquired at different pre-specified phases of the breathing cycle. The same procedures were repeated for a few patients a week to 10 days later. Lung patients could maintain comfortably an active breath-hold of 15 seconds near the end of normal inspiration. When suspended ventilation was applied during deep inspiration, the breath-hold period ranged from 25 seconds to 50 seconds. The suspended ventilation scans had minimal motion artifacts that were common in the planning CT acquired during quiet breathing with a helical scanner. Lung volumes from repeat suspended ventilation scans acquired at the same phase of breath-hold were within 5% of each other. Similar results were observed for the positions of the liver.

Thus, the present invention provides a method and apparatus for suspending ventilation which provides enhanced specificity of diagnosis and treatment.

We claim:

1. An apparatus for suspending ventilation in a patient and delivering radiation therapy to the patient during suspended ventilation, the apparatus comprising:
   an apparatus for identifying a specific air flow direction and lung volume of the patient;
   an apparatus for suspending patient ventilation at the specific air flow direction and lung volume, the apparatus for suspending patient ventilation including a ventilator assembly having a first selectively operable valve adapted to control inhalation of the patient and a second selectively operable valve adapted to control exhalation of the patient;
   an apparatus for administering radiation therapy during the suspension of patient ventilation; and
   an abort switch adapted to halt the apparatus for administering radiation therapy and open a closed one of the first and second selectively operable valves.

2. The apparatus of claim 1, wherein the ventilator assembly comprises a t-connector that includes the first selectively operable valve, the second selectively operable valve and a pneumotach.

3. The apparatus of claim 2, further comprising a computer that is operably associated with the ventilator assembly.

4. The apparatus of claim 3, further comprising:
   a first valve in fluid communication with the first selectively operable valve and operably associated with the computer;
   a second valve in fluid communication with the second selectively operable valve and operably associated with the computer; and
   wherein the pneumotach is operably associated with the computer.

5. The apparatus of claim 3, further comprising a display operably associated with the computer so that the display provides a readout of a cyclical lung volume trace and a target respiration level while the patient is breathing.

6. The apparatus of claim 5, further comprising a mirror for viewing a face of the patient, wherein the display is attached to the mirror.

7. The apparatus of claim 1, further comprising a mirror for viewing a face of the patient.

8. The apparatus of claim 1, wherein the first selectively operable valve is a one-way valve.

9. The apparatus of claim 1, wherein the second selectively operable valve is a one-way valve.

10. The apparatus of claim 8, wherein the second selectively operable valve is a one-way valve.

11. The apparatus of claim 1, further comprising a mouthpiece attached to the ventilator assembly.

12. An apparatus for suspending ventilation in a patient and delivering radiation therapy to the patient during suspended ventilation, the apparatus comprising:
   an apparatus for identifying a specific air flow direction and lung volume of the patient;
   an apparatus for suspending patient ventilation at the specific air flow direction and lung volume, the apparatus for suspending patient ventilation including a ventilator assembly having a selectively operable valve adapted to control both inhalation and exhalation of the patient;
   an apparatus for administering radiation therapy during the suspension of patient ventilation; and
   an abort switch adapted to halt the apparatus for administering radiation therapy and open the selectively operable valve.

13. The apparatus of claim 12, wherein the ventilator assembly comprises a pneumotach.

14. The apparatus of claim 13, further comprising a computer that is operably associated with the selectively operable valve and the pneumotach.

15. The apparatus of claim 14, further comprising a display operably associated with the computer so that the display provides a readout of a cyclical lung volume trace and a target respiration level while the patient is breathing.

16. The apparatus of claim 15, further comprising a mirror for viewing a face of the patient, wherein the display is attached to the mirror.

17. The apparatus of claim 12, further comprising a mirror for viewing a face of the patient.

* * * * *